United States Patent [19]

Quackenbush

[11] Patent Number: 4,840,623
[45] Date of Patent: Jun. 20, 1989

[54] MEDICAL CATHETER WITH SPLINED INTERNAL WALL

[75] Inventor: John Quackenbush, Hoover, Ala.

[73] Assignee: FBK International Corporation, Birmingham, Ala.

[21] Appl. No.: 151,061

[22] Filed: Feb. 1, 1988

[51] Int. Cl.⁴ ............................................. A61M 25/00
[52] U.S. Cl. .................................... 604/280; 138/108; 128/348.1
[58] Field of Search ................ 604/280, 288, 264, 93; 128/348.1; 138/108, 121, 119

[56] References Cited

U.S. PATENT DOCUMENTS

| 3,240,233 | 3/1966 | Johnston | 138/108 |
| 3,948,273 | 4/1976 | Sanders | 604/280 X |
| 4,579,555 | 4/1986 | Russo | 604/282 |

Primary Examiner—Stephen C. Pellegrino
Attorney, Agent, or Firm—Stanger, Michaelson, Reynolds, Spivak & Tobia

[57] ABSTRACT

Medical catheters with splined internal walls are disclosed as having sufficient rigidity to transmit torque from the proximal end to the distal end even over the long distances required for angioplast procedures. The splined geometry obviates the need for mesh layers characteristic of prior art guiding or diagnostic catheters and thus are significantly narrower and less costly to produce.

5 Claims, 1 Drawing Sheet

MEDICAL CATHETER WITH SPLINED INTERNAL WALL

FIELD OF THE INVENTION

This invention relates to small diameter medical catheters intended for insertion into the human body.

BACKGROUND OF THE INVENTION

Medical catheters for insertion into the human body are well known. It is also well known that such catheters have to be constructed such that the distal end of the catheter follows the movement of the proximal end. The manipulation of the distal end in response to the movement of the proximal end is important in order to be able to negotiate the catheter into bends and openings encountered along the insertion path.

The difficulties in providing a structure for the catheter which permits remote manipulation of the distal end are particularly intractable in long catheters as are required of angioplast guiding and diagnostic catheters which thread from the thigh to the heart. Such catheters are fifty to sixty inches long and have outside diameters of 8 to 9 French (a French=3.3 mils). Remote control of the distal end of such a catheter is difficult to achieve and therefore very expensive.

At the present time there are three approaches to making catheters which exhibit sufficient structural integrity to provide the torque necessary to manipulate the distal end as required. The first include a plastic tube encased in a wire mesh which in turn is encased in a plastic biocompatible tube. It is clear that catheter structures of this type require three separate operations to fabricate.

There are alternate techniques for making such catheters. One substitutes a nylon braid for the wire braid. Another substitutes a fiberglass-epoxy layer for the braid. It is clear that still three separate fabrication operations are needed. Commercially available diagnostic catheters of this type have at least a nine French outside diameter.

BRIEF DESCRIPTION OF EMBODIMENTS OF THE INVENTION

In accordance with the principles of this invention a catheter structure is provided which exhibits sufficient torque at the distal end to follow the manipulations of the proximal end. Yet the catheter includes no mesh or fiberglass-epoxy layer and thus can be extruded in one simple coextrusion step. In one embodiment, the catheter includes a splined interior wall with a biocompatible tube having a medium density block polyimide shell. The catheter can be made as a guiding catheter with a width of 7 to 8 French and as a diagnostic catheter permitting insertion of any commercially available balloon catheter where the catheter has an outside diameter of 4.5 to 7 French.

DETAILED DESCRIPTION

Figure 1:
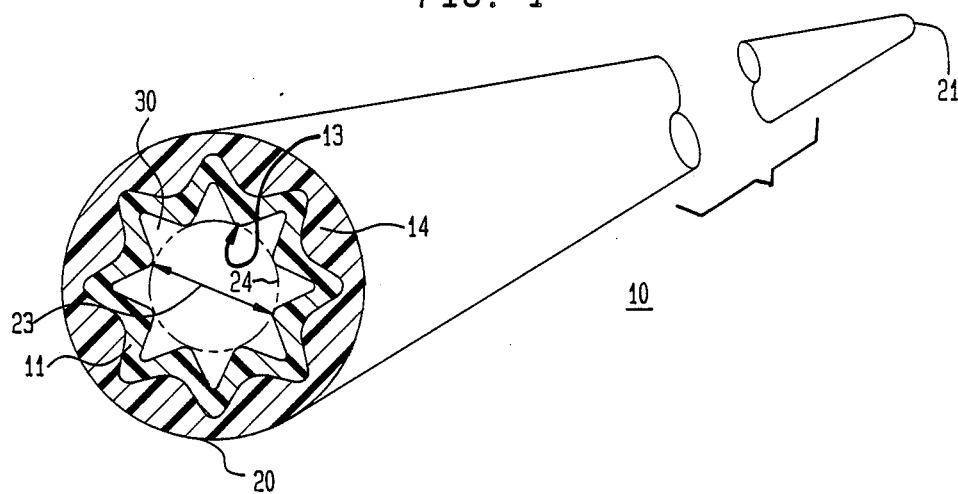
FIG. 1 is an enlarged schematic representation of a splined catheter tube in accordance with this invention showing a cross sectional view of the catheter.

FIG. 1 shows a catheter 10 having a splined internal wall. The catheter is shown in cross section at 11 in the Fig. and can be seen to include a splined inner layer 13 with an outer shell 14. The inner layer comprises, for example, a seventy five durometer, biocompatible, medical grade polyurethane polymer available commercially from Dow Chemical. The outer shell comprises, for example, a medium density, block polymer material (PBex6133 available from Aquitane).

The interior configuration of the inner layer imparts to the catheter the structure which permits the manipulation (rotation) of proximal end 20 to result in the equivalent manipulation of distal end 21 in the absence of meshes or fiberglass-epoxy layers characteristic of prior art catheters.

Both guiding catheters and diagnostic catheters can be made with splined interior walls in accordance with the principles of this invention. The guiding catheters for angioplast procedures is adapted to locate a stenosis and to determine if opaque fluids are to be introduced during a later diagnostic procedure when a balloon is to be inserted. The guiding catheter can be made with a splined interior wall having a width of four French rather than the minimum nine French width now available.

The diameter of the diagnostic catheter has to be relatively large to accommodate the balloon. Commercially available balloons for angioplast procedures have outside diameters of nine French. The diameter 23 of imaginary circle 24 which fits within the ridges of a splined interior wall in accordance with this invention measures 0.069 inch to accommodate the balloon. The outside diameter of catheter 10 need be only seven French, significantly smaller than the width of commercially available catheters for angioplast procedures.

Figure 2:
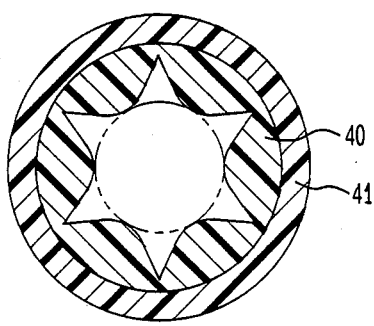
FIGS. 2 and 3 show enlarged alternative cross sections for the catheter of FIG. 1.
Figure 3:
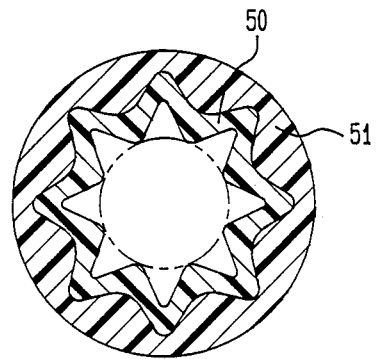

Catheter 10 can be formed in a single coextrusion process not possible with prior art mesh or fiberglass-epoxy catheters. Consequently, guiding or diagnostic catheters made in accordance with the principles of this invention are inexpensive as well as of relatively narrow width. FIGS. 2 and 3 show cross sections of alternative splined catheters as will be discussed more fully hereinafter.

Commercial catheters are adapted to exhibit a hook-shaped distal end resembling the head of a walking cane. The proximal end terminates in any one of a number of adaptors. Often, the adaptor includes a syringe connector. One suitable adaptor is commonly known as a "Laurlok" adaptor.

Figure 4:
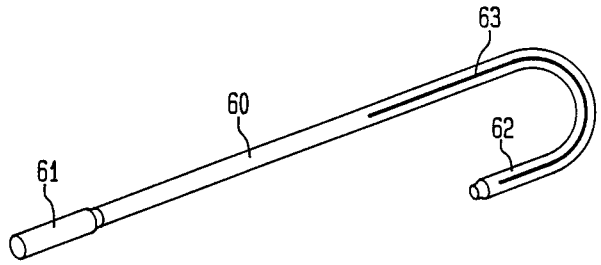
FIG. 4 is a schematic view of an end product catheter utilizing the splined tube of FIG. 1.

FIG. 4 shows a splined catheter 60 of FIG. 1 terminated at the proximal and distal ends with a Laurlok adaptor 61 and a hook 62 respectively. The shape of the distal end is imposed right after extrusion by a hook-shaped pin 63. Pin 63 is present during shipping and is removed prior to use. The distal end is straightened for insertion into the body and is thus biased to be maneuvered into apertures in say the aorta merely by rotation of the proximal end of the catheter.

The adaptor at the proximal end of the catheter may be adapted for inserting fluids or balloons as indicated above. Commercially available adaptors include ports suitable for this purpose and are completely adaptable for use with splined catheters in accordance with the principles of the present invention.

A splined catheter of the type shown in FIG. 4 was made with the materials identified above. The catheter had an internal diameter (23 of FIG. 1) of 0.069 inch to accept a balloon. A balloon was inserted and noted to be relatively free of friction due to the fact that the balloon contacted only the ridges of the internal wall. Thus, it was realized that a splined internal wall permitted an even smaller width catheter than had been expected because of the reduced friction encountered by the insertion and withdrawal of a balloon. Extra allowance is necessary for prior art catheters which have smooth internal walls which cause considerable friction during insertion and withdrawal of a balloon.

Another advantage of the splined catheter is that when a balloon is inserted in the catheter, it occupies the area encompassed by circle 24 of FIG. 1. There are areas between the balloon and between the ridges of the splined wall (i.e., see 30 of FIG. 1) which are available as lumens into which opaque fluids can be introduced without the necessity of a larger or additional catheter.

An experimental catheter with a splined internal wall as shown in FIG. 1 was manipulated to determine the torque generated at the distal end for test torques introduced at the proximal end. The test guiding and diagnostic catheters were sixty inches long with widths of four and seven French respectively. Corresponding tests were carried out with commercially available guiding and diagnostic catheters of equal length. The torques obtained at the distal ends of all the catheters were identical within experimental error of ±5%.

In the experimental splined catheters, the inner tube had a thickness of 0.030". The outer shell was of the biocompatible material noted above and had a non-uniform thickness with a minimum thickness of 0.015" and a maximum thickness of 0.025". Consequently, it is clear that both the inner tube and the outer shell had splined internal walls while the inner tube also had a splined outer wall.

Other splined structures were tested also and found to perform equally as well. FIGS. 2 and 3 show cross sections of two other catheter configurations as mentioned above. The inner tube 40 of FIG. 2 can be seen to have a splined internal wall and a smooth external wall whereas the outer shell 41 has smooth internal and external walls. Also, the ridges of the splined wall were sharper as shown.

FIG. 3 shows the cross section of another embodiment where each of inner tube and outer shell, 50 and 51 respectively, has a splined internal wall. The inner tube also has a splined outer wall but the outer shell has a smooth outer wall. It is noted that the thickness of the inner tube is constant in the embodiment of FIG. 1 but varying in the embodiments of FIGS. 2 and 3.

Test catheters were made with conventional coextrusion techniques using dies of a design and reduced size to produce the structures shown.

As significant as the reduction in catheter width and cost appears, the advantages in patient comfort and length of hospital stay is even more pronounced. It is clear that the use of the angioplast procedure is to be preferred over open heart surgery where recovery time is lengthy and where intensive care is necessary for an extended period. The cost reduction alone due to available angioplast procedures is tens of thousands of dollars when compared to the cost of open heart surgery. But even with an angioplast procedure, several days of intensive care are required after the procedure. Typically costs still exceed many thousands of dollars. Interestingly enough, intensive care is necessary because of the puncture wound made in the patients thigh to insert the catheter. A reduction in the size of the catheter because of the splined internal wall of the catheter in accordance with the principles of this invention reduces the size of the wound to one which can be treated with minimal topological attention virtually obviating the necessity for intensive care. The patient most likely could be released from the hospital on the day of the procedure.

What is claimed is:

1. A catheter adapted for insertion into the human body, said catheter including a flexible tube having an internal and an external wall, said internal wall having a splined configuration, and having an outer shell, said outer shell having an internal wall and an external wall, said internal wall of said outer shell having a geometry to match the geometry of the external wall of said inner tube and being integral herewith.

2. A catheter in accordance with claim 2 wherein said outer wall of said inner tube and said outer shell are circular.

3. A catheter in accordance with claim 1 wherein said outer wall of said inner tube is splined.

4. A catheter in accordance with claim 1 wherein said inner tube comprises 74 durometer biocompatible, medical grade polyurethane and said outer shell comprises a medium density, block polyimide material.

5. A catheter in accordance with claim 1 having proximal and distal ends, and manipulator means attached to said catheter at said proximal end.

* * * * *